(12) United States Patent
Chapman-Montgomery et al.

(10) Patent No.: US 7,723,064 B2
(45) Date of Patent: May 25, 2010

(54) METHODS FOR MONITORING PATIENTS FOR EFFICACY OF AN ANTIPLATELET THERAPY REGIMEN

(75) Inventors: E. Sabrinah Chapman-Montgomery, Croton on Hudson, NY (US); David Okrongly, Ridgefield, CT (US); Andrew McGregor Grant, Ulverton (CA); Charaf E. Ahnadi, Rock Forest (CA); Alan Wu, Palo Alto, CA (US); Andre Gervais, North Hatley (CA)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 61 days.

(21) Appl. No.: 11/658,367

(22) PCT Filed: Jul. 26, 2005

(86) PCT No.: PCT/US2005/026496

§ 371 (c)(1),
(2), (4) Date: Jan. 24, 2007

(87) PCT Pub. No.: WO2006/014958

PCT Pub. Date: Feb. 9, 2006

(65) Prior Publication Data

US 2008/0311606 A1    Dec. 18, 2008

Related U.S. Application Data

(60) Provisional application No. 60/591,025, filed on Jul. 26, 2004, provisional application No. 60/603,594, filed on Aug. 23, 2004.

(51) Int. Cl.
*C12Q 1/56*     (2006.01)
(52) U.S. Cl. ...................................................... 435/13
(58) Field of Classification Search ................... 435/13
See application file for complete search history.

(56) References Cited

U.S. PATENT DOCUMENTS

| | | | |
|---|---|---|---|
| 6,025,201 A | 2/2000 | Zelmanovic et al. | 436/63 |
| 2004/0038997 A1* | 2/2004 | Macey | 514/263.34 |
| 2004/0253637 A1 | 12/2004 | Buechler et al. | 435/7.1 |
| 2005/0095591 A1 | 5/2005 | Christopherson et al. | 435/6 |
| 2005/0136455 A1 | 6/2005 | Lehmann et al. | 435/6 |

OTHER PUBLICATIONS

Vidal C. et al. Flow Cytometry . . . Thrombosis Haemostasis 86(3)784-790, 2001.*

Ahnadi, C.E. et al., "Comparison of Two Methods to Assess Variability of Platelet response to Anti-Platelet Therapies in Patients with Acute Coronary Syndrome Undergoing Angioplasty", *Thrombosis Haemostasis*, 2004, 92(6), 1207-1213.

Vidal, C. et al., "Flow Cytometry Detection of Platelet Procoagulant Activity and Microparties inpatients with Unstable Angina Treated by PCA and Stent Implantation", *Thrombosis and Haemostasis*, 2001, 86(3), 784-790.

* cited by examiner

*Primary Examiner*—Ralph Gitomer
(74) *Attorney, Agent, or Firm*—Norm R. Pollack

(57) ABSTRACT

Methods are disclosed for monitoring patients utilizing Mean Platelet Component values during therapeutic intervention.

5 Claims, 9 Drawing Sheets

FIG. 5
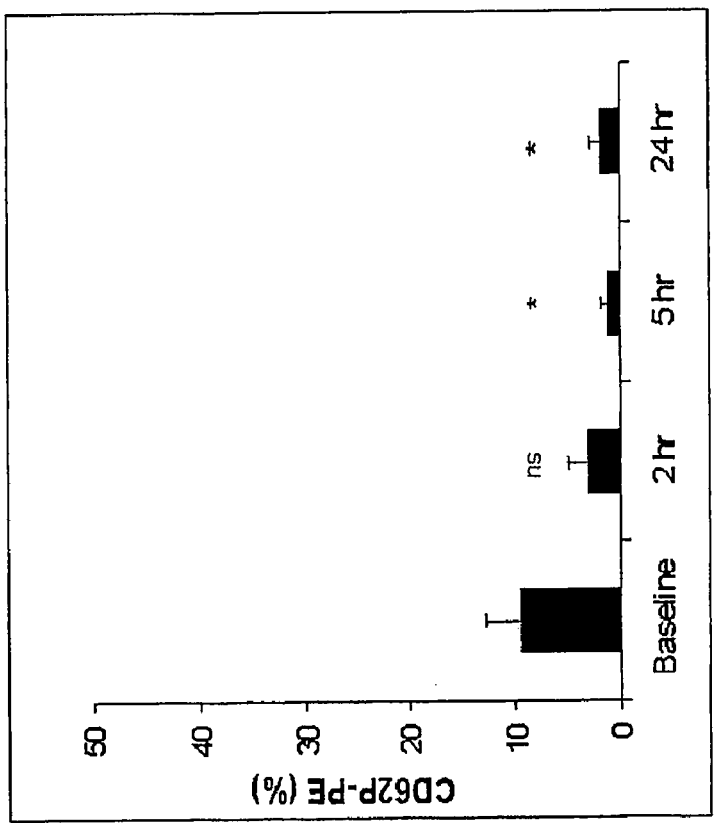
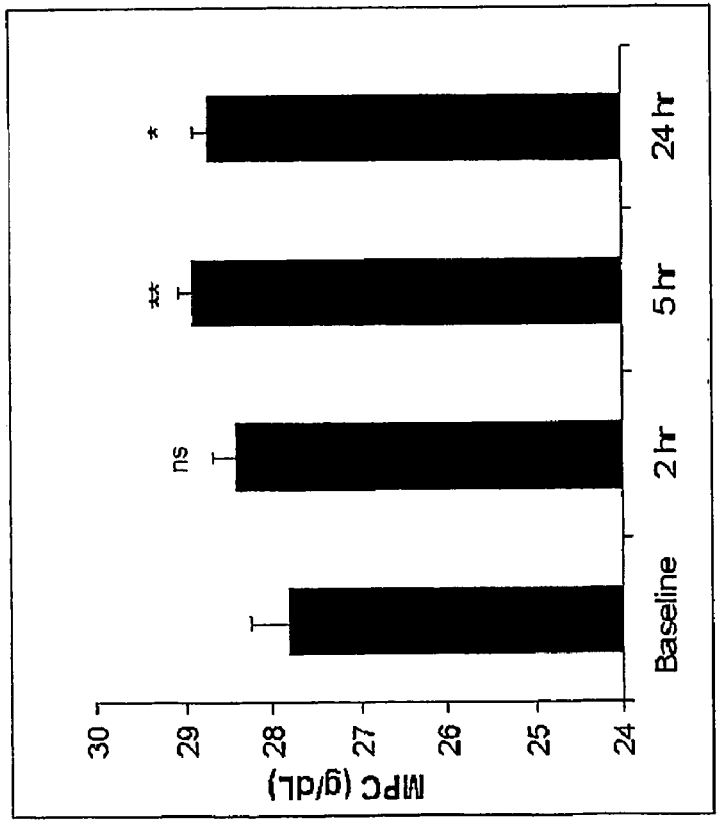

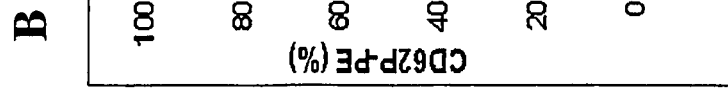
FIG. 8
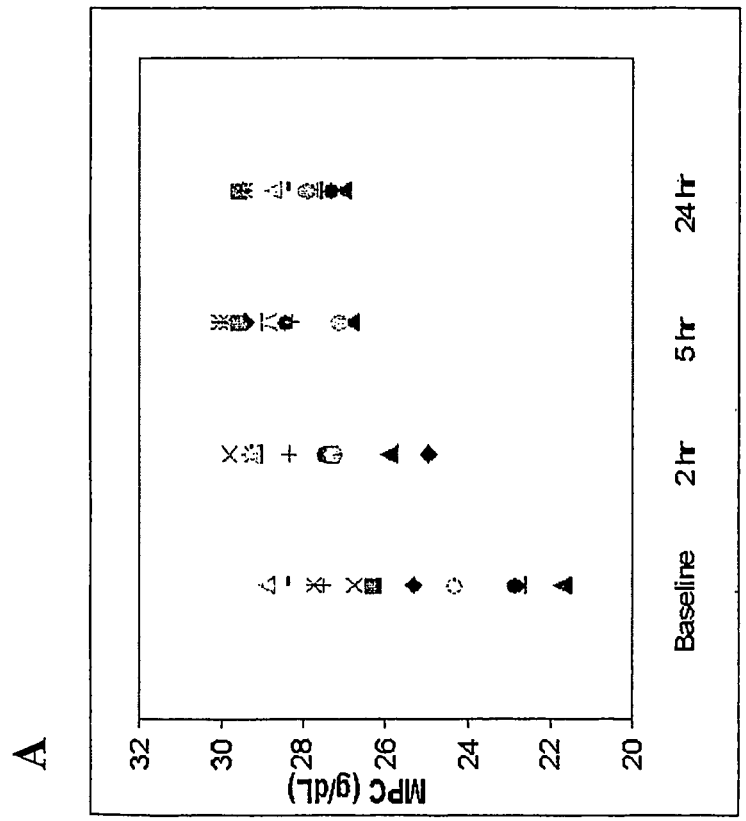

METHODS FOR MONITORING PATIENTS FOR EFFICACY OF AN ANTIPLATELET THERAPY REGIMEN

CROSS-REFERENCE TO RELATED APPLICATIONS

This application is the National Stage of International Application No. PCT/US2005/026496, filed Jul. 26, 2005, which claims the benefit of the filing date of U.S. Provisional Application No. 60/591,025, filed Jul. 26, 2004, and Provisional Application No. 60/603,594, filed Aug. 23, 2004, the disclosures of which are incorporated herein by reference in their entirety.

FIELD OF THE INVENTION

The invention provides methods for assessing thrombotic risk in patients, for predicting response to anti-platelet therapy, and for monitoring anti-platelet therapy in patients with platelet-affected disease states and/or in those undergoing angioplasty treatment.

BACKGROUND OF THE INVENTION

Platelets play a major role in the development of thrombus formation in patients with arterial thromboembolic diseases. Abnormal platelet behavior is associated with several pathological conditions, such as acute coronary syndrome ("ACS"), and in patients undergoing percutaneous transluminal coronary angioplasty ("PTCA"). Fitzgerald D. J. et al., *N. Engl. J. Med.* (1986) 315:983-989; Hamm C. W. et al., *J. Am. Coll. Cardiol.* (1987) 10:998-1006; Schultheiss H. P. et al., *Eur. J. Clin. Invest.* (1994) 24:243-247; Tschoepe D. et al., *Circulation* (1993) 88:37-42. Consequently, anticoagulant and anti-platelet therapies are widely used for cardiovascular disease patients. For example, treatment of ACS patients with aspirin, ADP receptor inhibitors, peptide and non-peptide glycoprotein IIb/IIIa (GPIIb/IIIa) receptor inhibitors, and other novel inhibitors of platelet function have been shown to significantly improve both short-term and long-term outcome by reducing the incidence of recurrent MI and death. Lewis H. D. et al., *N. Engl. J. Med.* (1983) 309:396-403; Jarvis B. and K. Simpson, *Drugs* (2000) 60: 347-377; Moshfegh K. et al., *J. Am. Coll. Cardiol.* (2000) 36:699-705; Rupprecht H. J. et al. *Circulation* (1998) 97:1046-1052; PRISM Study Group, *N. Engl. J. Med.* (1998) 338:1498-505; PRISM-PLUS Study Group, *N. Engl. J. Med.* (1998) 338:1488-1997; The EPIC Investigators, *N. Engl. J. Med.* (1994) 330:956-961; The CAPTURE Investigators, *Lancet* (1997) 349:1429-1435; Mascelli M. A. et al., *Circulation* (1998) 97:1680-1688. Inter-individual variation in response to the monoclonal antibody, abciximab, has been reported both in terms of extent and duration of inhibition of platelet function. Mascelli M. A. et al., *Circulation* (1998) 97:1680-1688; Bihour C. et al., *Arterioscler. Thromb. Vasc. Biol.* (1999) 16:212-9; Kleiman N. S. et al., *J. Am. Coll. Cardiol.* (1995) 26:1665-1671. Thus, anti-platelet therapies represent an important component in treatment regimens for numerous vascular pathologies.

Although high levels of platelet function inhibition has been reported to be associated with a decrease in the incidence of major adverse cardiac events, there is a clinical risk of thrombosis or bleeding associated with anti-platelet and anticoagulant treatments. Aguirre F. V. et al., *Circulation* (1995) 91:2882-2890. Currently, decisions to use anti-platelet treatments are based on clinical grounds due to the lack of acceptable methods to monitor platelet function in individual patients. The main problem with monitoring platelet function in patients is the artificial in vitro activation of platelets that occurs in conventional techniques. Several instruments have been developed to assess the global platelet response to anti-platelet therapy. A well-established method to assess platelet activation has been studied in whole blood using fluorescence flow cytometry. Michaelson, A. D. *Blood Coagul. Fibrinolys.* (1994) 5:121-131. The technique is specific and sensitive, since fluorescence measurements can detect as few as 0.8% activated cells. However, the technique is expensive, labor-intensive, and data analysis is imprecise. Further, in some patients, activated platelets lose their marker receptors but continue to circulate and function, which leads to missed detection with activation-specific fluorescence-labeled antibodies Michaelson, A. D. et al., *Methods* (2000) 21:259-270.

As a high level of platelet function inhibition has been reported to be associated with a decrease in the incidence of major adverse cardiac events, the question becomes whether clinicians should uniformly use aggressive and costly anti-platelet strategies without individual assessment of platelet status in patients with platelet-affected disorders. A simple and rapid method of early detection of platelet activation status without artificial activation of platelets would therefore be useful in identifying those particular patients who would benefit from platelet antagonist therapy, as distinguished from those in whom a material response to anti-platelet medicaments is not foreseen. Further, a simple, reliable and rapid method of monitoring treatment would be useful in optimizing safety and efficacy of anti-platelet therapy.

Platelets not only play an important role in the coagulation system, but are also an integral part of the inflammatory response. Shebuski R. J., Kilgore K. S. *J. Pharmacol. Exp. Therapeut.* (2002) 300:729-735; Aukrust P. et al., *Heart* (2001) 86:605-606; Freedman J. E. and J. Loscalzo. *Circulation* (2002) 105:2130-2132. The contribution of inflammation to the complications of acute ischemic syndromes and coronary revascularization has been increasingly recognized in recent years. Inflammation plays a pivotal role in vascular injury and repair. Accordingly, the inflammatory marker C-reactive protein (CRP) has emerged as a powerful predictor for cardiovascular disease, associated with future cardiovascular events in seemingly healthy subjects and with worse prognosis in acute coronary patient. Lagrand W. K. et al., *Circulation* (1999) 100:96-102; Ridker P. M. et al., *N. Engl. J. Med.* (2002) 347:1557-1565; Ridker P. M. et al., *N. Engl. J. Med.* (2000) 342:836-843; Ridker P. M. et al., *Circulation* (2000) 101:1767-1772.

Elevated circulating inflammatory markers, in particular CRP, have been associated with elevated risk for both short-term and long-term ischemic events among patients with unstable angina (Lindahl B. et al., *N. Engl. J. Med.* (2000) 343:1139-1147; Liuzzo G. et al., *N. Engl. J. Med.* (1994) 331:417-424), myocardial infarction (Tommasi S. et al., *Am. J. Cardiol.* (1999) 83:1595-1599), or those undergoing percutaneous angioplasty (Buffon A. et al., *J. Am. Coll. Cardiol.* (1999) 34:1512-1521; Versaci F. et al., *Am. J. Cardiol.* (2000) 85:92-95; Chew D. P. et al., *Circulation* (2001) 104(9):992-997). Elevated pre-angioplasty CRP levels predicted an increased rate of procedural and in-hospital complications (Buffon A. et al., *J. Am. Coll. Cardiol.* (1999) 34:1512-1521) an increased risk of death or MI at 1 month follow-up (Chew D. P. et al., *Circulation* (2001) 104(9):992-997), and 6 months follow-up (Heeschen C. et al., *J. Am. Coll. Cardiol.* (2000) 35:1535-1542) compared with those patients who have a normal CRP. At 1-year follow-up, clinical restenosis developed in 63% of patients with high pre-angioplasty CRP levels versus only 27% of those with values in the reference range.

In fact, elevation of CRP before early revascularization for non-ST-elevation ACS predicts mortality for up to 5 years. Mueller C. et al., *Circulation* (2002) 105; 1412-1415.

The association between platelet activation and markers of inflammation has been reported in different pathologies. In general, inflammation can promote thrombus formation and can enhance clot stability. The relationship between systemic infection or inflammation and an increased risk of thrombotic diseases has recently raised renewed interest. In patients with acute thrombotic stroke, Toghi et al. showed that platelet aggregation induced by ADP was significantly higher where CRP levels were elevated compared to control donors with normal CRP levels. The data suggest that platelet function may be, in part, related to stroke onset in patients with increased CRP levels. Toghi H. et al., *Thromb. Res.* (2000) 100:373-379. In hypercholesterolemia, in vivo platelet activation measured by soluble P-selectin and urinary 11-debydro-TxB$_2$ excretion, are associated with increased sCD40L levels (Cipollone F. et al., *Circulation* (2002) 106:399-402) and IL-1β and CRP (Ferroni P et al., *Circulation* (2003) 10814:1673-1675), markers of systemic inflammation. In obese women, increased platelet activation was driven by high CRP and both were reversible with loss of weight (Davi G. et al., *JAMA* (2002) 288:2008-2014).

These inflammatory processes may be reciprocally affected by platelet activation. Toghi H. et al., *Thromb. Res.* (2000) 100:373-379; Neumann F.-J. et al., *Circulation* (1997) 95:2387-2394. Platelet activation can increase inflammation through several mechanisms. Platelets release a wide range of growth factors and inflammatory mediators from intracellular storage organelles. Products of activation may aid neutrophil accumulation and enhance inflammation. Activated leukocytes and platelets potentiate each others' effects. The important mediators released by platelets are P-selectin (CD62p), CD40p, platelet activating factor, macrophage chemotactic factor-1, interleukin-1, thrombospondin and fibronectin. These mediators are rapidly expressed by activated platelets. Weyrich A. S. et al., *J. Clin. Invest.* (1996) 97:1525-1534; Carlos T. M. et al., *Blood* (1994) 84:2069-207; Zimmerman G. A. et al., *Crit. Care Med.* (2002) 30:294-301; Valles J et al., *Blood* (2002) 99:3978-3984; Sarma J. et al., *Circulation* (2002) 105:2166-2171; O'Brien K. D. et al., *Circulation* (1996) 93:672-682. Davi et al. reported a biochemical mechanism suggesting that a low-grade inflammatory state may be the primary trigger of thromboxane-dependent platelet activation mediated through enhanced lipid peroxidation. Davi G. et al., *JAMA* (2002) 288:2008-2014. Other mechanisms, such as a direct proinflammatory effect of CRP, are likely to amplify and sustain the relationship between systematic inflammation and platelet activation. Pasceri V. et al., *Circulation* (2000) 102:2165-2168.

Increased level of basal platelet activity has been correlated with adverse events. Stemhubl S. R. et al., *Circulation* (2001) 103:2572-2578. It is hypothesized that the baseline platelet activation status may be predictive of future platelet activity accompanied by vascular complications. Gurbel P. A. et al., *Thrombosis Res.* (2000) 99:105-107; Gurbel P. A. et al., *Scand. Cardiovasc. J.* (2000) 34:53-58. There is an urgent need for identifying patients who may be susceptible to future untoward platelet events associated with vascular complications so that these patients can be earmarked for more aggressive anti-platelet regimens. Indeed, Ridker et al. showed in the Physician's Health Study that patients at the highest level of risk, as measured by CRP, derive the most benefit from effective anti-platelet therapy. See Ridker P. M. et al., *N. Engl. J. Med.* (1997) 336:973-979.

There is a need in the art for a rapid, simple test for platelet activation that can be used in a dynamic fashion to detect platelet activation and predict vascular problems as well as to monitor platelet activation in patients undergoing anti-platelet therapy and/or angioplasty.

SUMMARY OF THE INVENTION

The present invention uses the detection of MPC as well as early markers such as the inflammation marker CRP to assess platelet activity in discrete patients, in order to ascertain interindividual heterogeneity of platelet activation. These results are useful for early apprehension of susceptibility to vascular pathological events, to predict response to platelet antagonist therapies, to generate individualized anti-platelet regimens, and to monitor patients once therapy has been initiated, either concurrently with percutaneous angioplasty or in isolation.

Provided are methods for early detection of a platelet-affected disease state in a patient, including the steps of determining the Mean Platelet Component (MPC) values in patient blood samples, using the MPC values to determine baseline platelet activation status, and correlating the discovered platelet activation status to the presence or absence of a platelet-affected disease state. The inventive methods are useful for predicting susceptibility to a broad range of vascular pathologies, including, inter alia, acute coronary syndrome (e.g., unstable angia ("UA") and non-ST-segment elevation myocardial infarction ("NSTEMI")), stroke, ischaemic complications of peripheral vascular disease, deep vein thrombosis, myocardial infarction, coronary artery disease, cerebrovascular disease, peripheral arterial disease, diabetes mellitus, diabetic retinopathy, atrial fibrillation, congestive heart failure, pulmonary embolism, or other related disease states. Also provided are methods that additionally comprise using an early marker of patient risk to obtain an additional early indication of a platelet-affected disease state. In some embodiments, the early marker is C-reactive protein.

Another aspect of the present invention is directed to methods for predicting response to anti-platelet therapy in patients with a platelet-affected disease state, including the steps of determining the MPC values in patient blood samples, using these MPC values to determine baseline platelet activation status, and correlating high baseline platelet activation status with appropriateness of anti-platelet therapy. Such methods are useful for, inter alia, identifying patients who would be most likely to benefit from more aggressive anti-platelet regimens and predicting the efficacy of such treatments in individual patients.

Also provided are methods for monitoring patients during an anti-platelet therapy regimen comprising determining the MPC values in patient blood samples, and using these MPC values to determine whether the levels of platelet activation are reduced by the platelet antagonist therapy, thereby indicating the production of a therapeutic effect. In some embodiments these method also include determining the expression of an early marker of patient risk in patient blood samples, and in certain embodiments, the early marker is C-reactive protein. In some other embodiments, the preceding method is performed for blood samples retrieved from a patient who is also undergoing angioplasty in addition to an anti-platelet therapy regimen.

Further objects and advantages afforded by the invention are apparent from the detailed description provided below.

BRIEF DESCRIPTION OF THE DRAWINGS

FIGS. 5 and 6 give mean results of a test involving inhibition of circulating activated platelets by Clopidogrel or by Abciximab treatment, respectively.

FIG. 7 shows individual changes in MPC and CD62P-PE during Clopidogrel treatment of patients with no detectable baseline or subsequent increase in platelet activity (7A (MPC) and 7B (CD62P-PE)) and FIG. 8 shows those patients displaying increased baseline platelet activity, followed by a decrease after treatment and angioplasty (8A (MPC) and 8B (CD62P-PE)).

DETAILED DESCRIPTION OF ILLUSTRATIVE EMBODIMENTS

Figure 1:
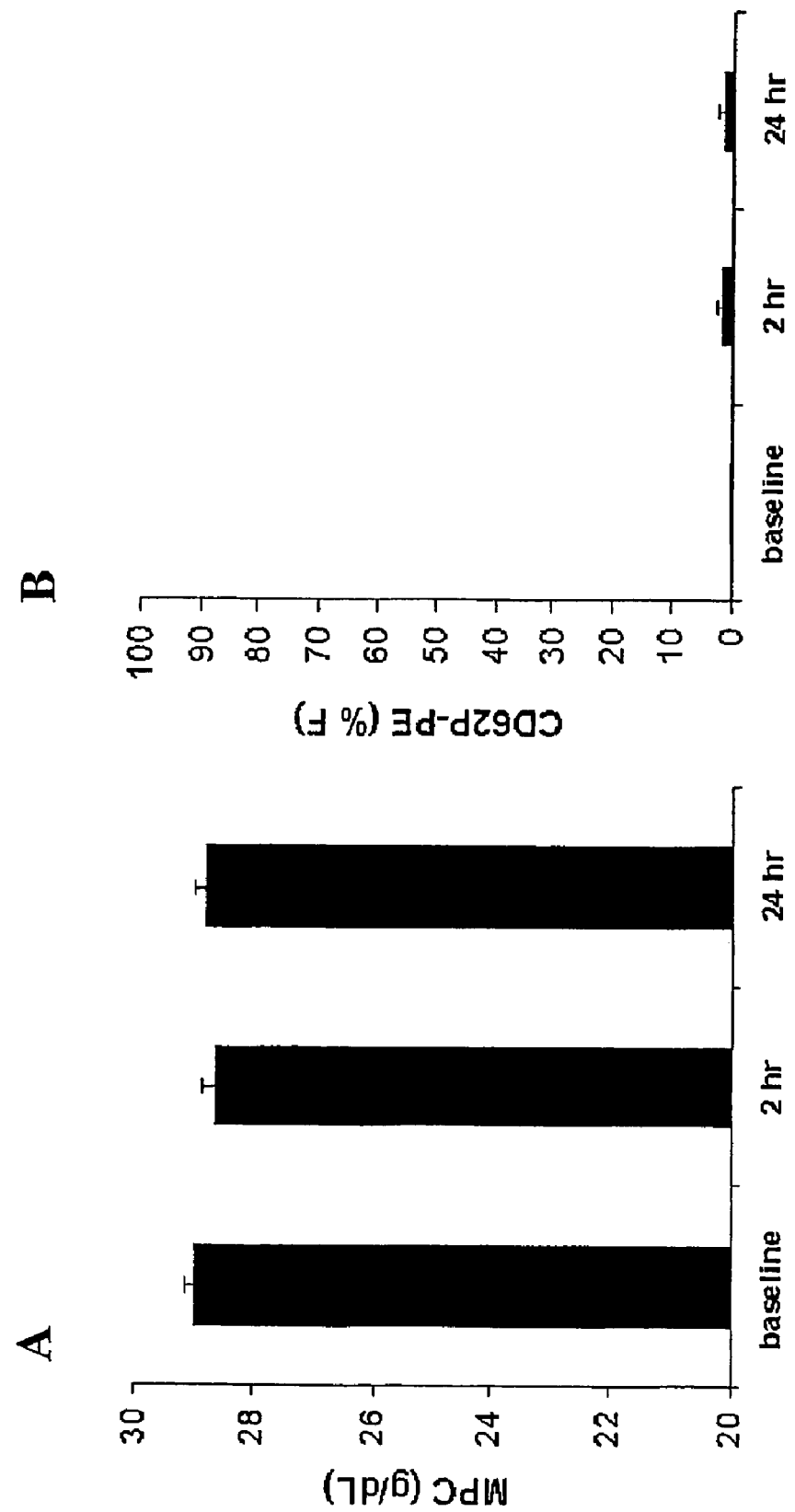
FIGS. 1 and 2 disclose basal platelet activation status for two distinct groups of patients (those that display no detectable platelet activation before or after platelet antagonist treatment, and those that demonstrate high baseline platelet activity and positive response to anti-platelet therapy, respectively) as assayed by MPC and CD62P expression.

The reference works, patents, patent applications, and scientific literature that are referred to herein are hereby incorporated by reference in their entirety to the same extent as if each was specifically and individually indicated to be incorporated by reference. Any conflict between any reference cited herein and the specific teachings of this specification shall be resolved in favor of the latter.

As employed above and throughout the disclosure and claims, the following terms and abbreviations, unless otherwise indicated shall be understood to have meanings as defined herein.

"Anti-platelet" and "platelet antagonist" therapies are those that inhibit platelet activity, including, inter alia, aggregation, accumulation, adhesion, and/or cohesion. Nonlimiting examples of such in vivo therapies include treatment with aspirin, Clopodigrel, Abciximab, ADP-receptor inhibitors, peptide and non-peptide glycoprotein IIb/IIIa (GPIIb/IIIa) receptor inhibitors, alpha2beta1 integrin inhibitors, glycoprotein VI integrin inhibitors, and other novel inhibitors of platelet function. It should be understood that the usefulness of the instant methods is not dependent on the identity or mechanism of action of the chosen inhibitor of platelet activity, and therefore the inventive methods may be employed without regard to the type of anti-platelet or platelet antagonist therapy that is selected.

A "material response" to platelet antagonist treatment is one which produces a therapeutically significant physiological change in local or systemic platelet activation status.

As used herein, "platelet-affected disease" refers to a disorder characterized by abnormal levels of platelet activation.

As used herein, "reference normal MPC value" means a value for MPC that would be obtained for a normal healthy individual. For example, but not by way of limitation, the value may be obtained from a normal, healthy control sample (e.g., blood sample) or it may be a standard reference MPC value.

As used herein, the terms "treatment" or "therapy" (as well as different word forms thereof) includes preventative (e.g., prophylactic), curative or palliative treatment.

The term "vascular system" refers to the vessels and tissue that carry or circulate fluids in the body of an animal, including but not limited to the heart, blood vessels, lymphatic, pulmonary, and portal systems.

The phrases "vascular disease," "vascular disorder," "vascular condition," "vascular pathology," and the like, refer to bodily states affecting the channels and tissue that carry body fluids, such as, but not limited to stroke, deep vein thrombosis (DVT), myocardial infarction, coronary artery disease, cerebrovascular disease, peripheral arterial disease, diabetes mellitus, diabetic retinopathy, atrial fibrillation, congestive heart failure, acute coronary syndrome (e.g., UA/NSTEMI), stroke, pulmonary embolism, and ischemic complications of peripheral vascular disease.

"Subject" or "patient" refers to an embryonic, immature, or adult animal, particularly mammals including humans, that is treatable with the compositions, and/or methods of the present invention.

In the present disclosure the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minute(s), "h" means hour(s), "g" means gram(s), "mg" means milligram(s), "µg" means microgram(s), "kg" means kilogram(s), "eq" means equivalent(s), "dL" means deciliter(s), "µL" means microliter(s), "mL" means milliliter(s), "M" means molar, "mM" means millimolar, and "SD" means standard deviation.

The invention provides methods for early detection of a platelet-affected disease state in a patient, comprising the steps of determining the Mean Platelet Component (MPC) values in patient blood samples, using the MPC values to determine baseline platelet activation status, and correlating the discovered platelet activation status to the presence or absence of a platelet-affected disease state, wherein a low MPC value generally corresponds to increased platelet activation. In some embodiments, a normal value of MPC for a healthy adult is about 25-30 g/dL. In other embodiments, a normal value of MPC for a healthy adult is about 26-29 g/dL. In still other embodiments, a normal value of MPC for a healthy adult is about 27-28 g/dL.

The ADVIA 120 Hematology System's platelet analysis is an automated method that uses both volume and density measurements to derive an accurate platelet count, as well as a platelet density value, MPC. In this study and others, MPC has been shown to be increased in inactivated platelets and decreased in activated platelets (Macey M. G. et al., *Cytometry* (1999)38:250-255; Chapman E. S. et al., *Thromb. Haemost.* (2003) 89:1004-1015; Ahnadi C. E. et al., *Thromb. Haemost.* (2003) 90:940-948). The measurement of MPC does not require specimen preparation, platelet activation specific receptors, or activation-specific receptor labels. The MPC values have shown very good inverse correlation with the percentage of platelets expressing CD62P antigen as detected by fluorescent flow cytometry after activation by thrombin. Ahnadi C. E. et al., *Thromb. Haemost.* (2003) 90:940-948. MPC values may be obtained as described in, for example, U.S. Pat. Nos. 6,025,201; 5,817,519; and 6,524,858, which are incorporated by reference herein.

The methods are useful for predicting susceptibility to a broad range of vascular pathologies, including, but not limited to, acute coronary syndrome (e.g., UA/NSTEMI), stroke, ischemic complications of peripheral vascular disease, deep vein thrombosis, myocardial infarction, coronary artery disease, cerebrovascular disease, peripheral arterial disease, diabetes mellitus, diabetic retinopathy, atrial fibrillation, congestive heart failure, pulmonary embolism, or other related disease states.

Also provided are methods that additionally comprise assessing the expression of an early marker of vascular disease to obtain an additional early indication of a platelet-affected disease state. In such embodiments, the expression level of the early marker is determined before tissue damage occurs. In some embodiments, the early marker is at least one of C-reactive protein (CRP), B-type natriuretic peptide (BNP), myeloperoxidase, metalloproteinase-9, soluble CD40 ligand, pregnancy-associated plasma protein A, choline, ischemia-modified albumin, unbound free fatty acids, glycogen phosphorylase isoenzyme BB, and placental growth factor. In some embodiments the early marker is C-reactive protein. In other embodiments, the early marker is BNP.

Many techniques are known to analyze the level of expression of specific genes in cells and tissues, including but not limited to quantitative PCR, rtPCR, RNA diagnosticing, SAGE (sequential analysis of gene expression), differential display, and microarrays. Such techniques are well known in the art and many protocols are known to skilled artisans for practicing such technology. Reference materials include Ausubel et al., CURRENT PROTOCOLS IN MOLECULAR BIOLOGY, John Wiley & Sons, New York, 1998; Sambrook et al., MOLECULAR CLONING:A LABORATORY MANNUAL, 2d Ed., Cold Spring Harbor Laboratory Press, Plainview, N.Y., 1989; and Kaufman et al., Eds., HANDBOOK OF MOLECULAR AND CELLULAR METHODS IN BIOLOGY AND MEDICINE, CRC Press, Boca Raton, 1995.

In one embodiment of the present invention, genes, which ate differentially expressed in association with a disease, specifically a platelet-affected disease, are identified using the methods known to those of skill in the art to analyze gene expression. One skilled in the art, in view of the present disclosure, recognizes that the expression of these genes serves as early markers of vascular disease. Such gene expression analysis may be conducted on the peripheral blood samples used to determine MPC values. Positive values (i.e., expression of the genes) indicates an increased risk for vascular complications. When viewed in conjunction with a low MPC value, the result indicates that the patient would be susceptible to coronary events and further vascular disease or damage.

Another aspect of the present invention is directed to methods for predicting response to anti-platelet therapy in patients with a platelet-affected disease state, including the steps of determining the MPC values in patient blood samples, using these MPC values to determine baseline platelet activation status, and correlating high baseline platelet activation status with appropriateness of anti-platelet therapy. Such methods are useful for, such uses as identifying patients who would be most likely to benefit from more aggressive anti-platelet regimens and predicting the efficacy of such treatments in individual patients.

The invention also provides methods for monitoring patients during an anti-platelet therapy regimen comprising determining the MPC values in patient blood samples over time, and determining whether these MPC values increase over time, indicating that the levels of platelet activation in these patients are reduced by the platelet antagonist therapy (i.e., indicating a therapeutic effect).

In some embodiments the method of determining whether a patient would benefit from anti-platelet therapy would also include determining the expression of an early marker of vascular disease in patient blood samples. In certain embodiments, the early marker is at least one of C-reactive peptide, myeloperoxidase, metalloproteinase-9, soluble CD40 ligand, pregnancy-associated plasma protein A, choline, ischemia-modified albumin, unbound free fatty acids, glycogen phosphorylase isoenzyme BB, placental growth factor or brain natriuretic peptide (BNP). In some embodiments, at least one of the early markers is C-reactive protein. In other embodiments, at least one of the early markers is BNP.

In these embodiments a positive result from an early marker (i.e., expression of the early marker gene) in conjunction with a low MPC value indicates that the patient has an elevated risk for vascular disease or coronary complications and would be a candidate for anti-platelet therapy.

In the embodiments in which MPC values are taken over time to measure the therapeutic effect of anti-platelet therapy, the method may be used for patients undergoing angioplasty. In other embodiments, the method may be used for patients undergoing angioplasty apart from any anti-platelet therapy.

MPC may be measured using the ADVIA 120 Hematology System technology which offers two-dimensional platelet analysis on an automated analyzer that in addition to measuring the conventional hematologic indices, and also provides activation-related information about platelets. The ADVIA 120 System's platelet analysis is an automated process that uses both volume and density measurements to derive an accurate platelet count, as well as a platelet density value, MPC. Platelet analysis by this system detects two light scattering signals on each platelet analyzed (typically 2,500 platelets are analyzed per sample) and converts those into platelet volume and density. The platelet density parameter, mean platelet component concentration (MPC) is reported in 30 seconds. A decrease in platelet density, measured by a reduction in MPC is indicative of platelet activation. MPC also shows, in vitro, excellent correlation with the well-defined fluorescence marker, CD62P-Phycoerythrin (CD62P-PE) Macey M. G. et al., *Cytometry* (1999) 38:250-255; Chapman E. S. et al. *Thromb. Haemost.* (2003) 89:1004-1015; Ahnadi C. E. et al. *Thromb. Haemost.* (2003) 90:940-948. The use of the MPC parameter may therefore provide rapidly available platelet activation test results.

MPC values in normal adults is in the range of about 25 to 30 g/dL. In some embodiments, a normal value is considered 27.2±1.3 g/dL. A lower MPC value than normal corresponds to an increase in platelet activation. Thus, a goal of anti-platelet therapy is to raise the MPC value to normal or to a level of at least about 25 g/dL.

MPC values are easily obtained from whole blood samples using the ADVIA 120 Hematology System in accordance with the manufacturer's instructions. MPC values can be obtained over time during an anti-platelet therapy regimen, for example, to monitor the course of anti-platelet therapy. It is believed that the anti-platelet therapy inhibits activation of platelets and thus, raises the MPC values in the treated patient. Thus, a physician with ordinary skill in the art would be able to monitor the progress of the anti-platelet therapy by correlating a rise in MPC values with efficacy in lowering platelet activation in the patient. A decline of MPC values or unchanged low MPC values would indicate that the anti-platelet therapy is not having the desired effect of the patient and that the patient may be at increased risk for coronary complications.

EXAMPLES

The present invention is further defined in the following examples. It should be understood that these examples, while indicating certain embodiments of the invention, are given by way of illustration only, and should not be construed as limiting the appended claims. From the preceding discussion and these examples, one skilled in the art may ascertain the essential characteristics of the instant invention, and without departing from the spirit and scope thereof, can make various changes and modifications of the invention to adapt it to various usages and conditions.

Example 1

Basal Platelet Activation Levels in Patients with Acute Coronary Syndrome

The following study determined a relationship between platelet activation and elevated baseline platelet-activation markers in patients with acute coronary syndrome (e.g., UA/NSTEMI). Baseline activation status as measured by MPC is predictive of future platelet activity and vascular complications in the patients. The baseline activation status as measured by MPC therefore also identifies individual patients who would be most likely to benefit from an anti-platelet regimen.

Blood was drawn from patients before and after anti-platelet therapy and angioplasty. Platelet activation was evaluated by expression of CD62P (P-selectin) measured by flow cytometry and by the platelet density parameter, mean platelet component (MPC) concentration measured on the ADVIA 120 Hematology System. MPC drops with platelet activation and is associated with decreased platelet density linked to platelet degranulation. The inflammation process was evaluated by the measurement of high-sensitivity C-reactive protein (CRP).

Patients. A total of 44 patients who underwent elective percutaneous coronary angioplasty and stenting were evaluated. The study was approved by the institutional committee on human research. Patients were enrolled in the study after informed consent had been obtained. Their baseline variables including age, gender, smoking history, risk factors, antecedents and medication were documented. These patients received either a loading dose of Clopidogrel (300 mg) before the beginning of the PTCA procedure followed by 75 mg daily for 1 month or intravenously a 0.25 mg/kg, bolus of Abciximab before the beginning of the PTCA procedure followed by a 0.125 µg/kg/mn infusion for 12 h.

Blood collection. Blood was drawn with a 21-gauge needle into EDTA (5 mM) tubes, mixed immediately with the anticoagulant and avoiding frothing during the mixing procedure. The first 1-2 ml of blood were discarded to avoid the effects of traces of thrombin generated during venipuncture. Serum was collected for CRP measurements. Whole blood specimens for measurement of the ADVIA® 120 Hematology System platelet parameters and flow cytometry analysis were taken prior to baseline, 2 hours, and 24 hours after administration of anti-platelet therapy and PTCA. For platelet activation measurements, all specimens were processed within 1 h after blood collection.

CRP measurement. CRP was measured in serum by the high sensitivity CRP assay using a nephelometric technique with a Behring Nephelometer ProSpec System (Dade Behring, Deerfield, Ill.). CRP was determined prior to (baseline), 2 hours, and 24 hours after administration of anti-platelet therapy and PTCA.

Fluorescence flow cytometry analysis. Whole blood samples were fixed with methanol-free paraformaldehyde (final concentration 0.5%). Fixed blood (5 µl) was incubated at room temperature for 15 min in the dark with monoclonal antibody CD61a-FITC. (10 µl) to identify the platelets and CD62P-PE (10 µl) to measure the expression of P-selectin. Platelets labeled with FITC or PE-conjugated isotype control antibody were used as control for nonspecific staining.

Samples were diluted to 1 ml with PBS. FACScan calibration and compensation were performed as recommended by the manufacturer. Five thousand (5,000) CD61a positive events were acquired on the FACScan flow cytometer (Becton Dickinson, Franklin Lakes, N.J.) equipped with Lysis II software. Data analysis was performed using a threshold based on the FITC-fluorescence correlating to the platelet specific binding of CD61a-FITC antibodies. A gate was drawn around the fluorescent platelet population. The CD61a-FITC labeled platelets that were also positive for PE-conjugated activation marker antibody (CD62P) was quantitated and presented as percentage of positive events.

Bayer ADVIA 120 automated hematology system platelet density measurement. The two-dimensional platelet method is based on the analysis of platelets in whole blood by flow cytometry using the ADVIA 120. The system was standardized and calibrated as per the manufacturer's instructions. The ADVIA 120 Hematology System was quality-controlled using TESTpoint Hematology control reagents (Bayer HealthCare, LLC, Tarrytown, N.Y.). The whole blood specimens anticoagulated with EDTA were processed within 1 h after specimen collection. The ADVIA 120 platelet density parameter, MPC, has previously been shown to be in the normal range in resting platelets and decreased in activated platelets. See Macey M. G. et al., *Cytometry* (1999) 38:250-255; Chapman E. S. et al., *Thromb. Haemost.* (2003) 89:1004-1015; Ahnadi C. E. et al., *Thromb. Haemost* (2003) 90:940-948. In this study, MPC determinations were acquired as a measure of platelet activation at baseline, 2 hours, and 24 hours after anti-platelet drug therapy.

Statistical analysis. Data are given as mean±standard deviation (SD) when applicable The differences between baseline and post-treatment values were analyzed with the paired t-test. Chi-square test was used to analyze the relationship between CRP and platelet activation, p-values <0.05 were considered statistically significant.

Results

Baseline characteristics of patients. Clinical and demographic features are shown in Table 1. All patients had symptomatic coronary artery disease, unstable angina, and/or myocardial infarction. The majority of patients were receiving aspirin.

TABLE 1

| Baseline clinical characteristics | |
|---|---|
| | All patients (n = 44) |
| Sex | M: 34; F: 10 |
| Age (years, mean ± SD) | 59.5 ± 11 |
| Diagnosis | n (%) |
| Unstable angina | 31 (71%) |
| Myocardial infarction | 12 (27%) |
| Stable coronary artery disease | 1 (2%) |

TABLE 1-continued

Baseline clinical characteristics

| | All patients (n = 44) |
|---|---|
| Medication received before | n (%) |
| Aspirin | 39 (88%) |
| Oral anticoagulant | 26 (59%) |
| History | n (%) |
| Hypertension | 21 (48%) |
| Diabetes | 4 (9%) |
| Current Smokers | 16 (36%) |

Platelet activation. Individually, platelet activation determinations in patients receiving Clopidogrel or Abciximab showed two distinct groups as assayed by MPC and CD62P expression. The results of these assays provided a novel means of distinguishing among patient groups—two groups were defined according to the basal platelet activation status their potential materially to respond to anti-platelet treatment: Group 1 patients showed no detectable platelet activation before or after treatment (FIGS. 1A and B), and Group 2 patients demonstrated a high baseline platelet activity and positive response to anti-platelet treatment (FIGS. 2A and B).

Figure 2:
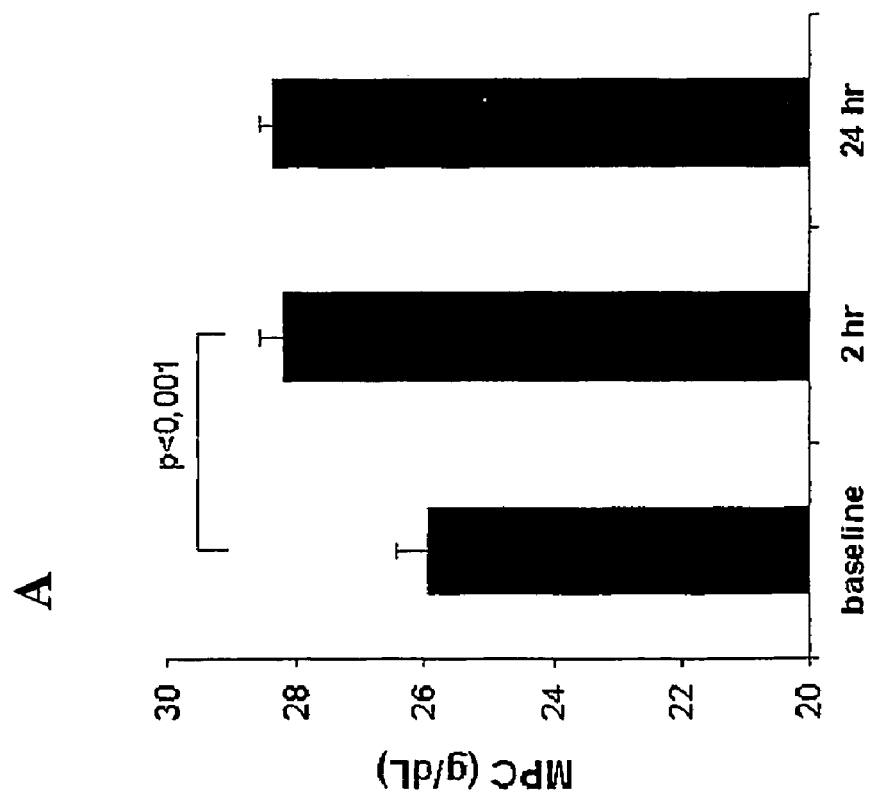

Patients who exhibited high baseline platelet activation (Group 2, n=16) responded to Clopidogrel or Abciximab treatment as indicated by a decrease in CD62P percent positive expression at time points after treatment (24.3±19.9%, 1.8±2.8%, and 1.2±1.5%, $p<0.001$, for baseline, 2 h, and 24 h, respectively) (FIG. 2B). A concomitant increase in MPC values (25.94±2.10 g/dL, 28.21±1.39 g/dL, and 28.35±0.92 g/dL, $p<0.001$, for baseline, 2 h, and 24 h, respectively) was seen in those patient samples (FIG. 2A).

The status of platelet activation in Group 1 patients (n=26) was detected as normal before treatment based on CD62P expression, as well as MPC levels. Those patients were unresponsive to treatment (FIGS. 1A and B). Measurement of CD62P-PE, the gold standard-fluorescence flow cytometric method for platelet activation shows very good correlation with MPC. However, the CD62P method is very expensive and labor intensive. In view of the correlation of MPC and CD62P, these results indicate that the rapid MPC assay alone is capable of providing accurate predictions as to patient responsiveness to platelet antagonist therapy.

CRP variation. Table 2 shows CRP levels of the two groups, based on the presence or absence of platelet activation, before, 2 h, and 24 h after percutaneous transluminal coronary angioplasty ("PTCA") and drug administration. The serum concentration of CRP was markedly increased in the group with elevated platelet activation. In both groups, CRP levels were increased at 24 h after PTCA in 19 patients (43%) compared to the baseline. This result is concordant with several studies which reported that angioplasty procedure by itself produces a pro-inflammatory state and is accompanied by a rise in CRP levels.

TABLE 2

| | CRP (mg/L) | | |
|---|---|---|---|
| | Angioplasty and anti-platelet therapy | | |
| | baseline | 2 h after | 24 h after |
| Group 1 | 6.02 ± 8.64 | 5.41 ± 8.03 | 8.07 ± 7.49* |
| | (0.53-43.25) | (0.42-41.40) | (0.57-34.80) |
| Group 2 | 19.89 ± 33.14 | 18.92 ± 32.13 | 22.01 ± 40.08 |
| | (0.40-138) | (0.33-135) | (0.60-168) |

*$p < 0.05$

Figure 3:
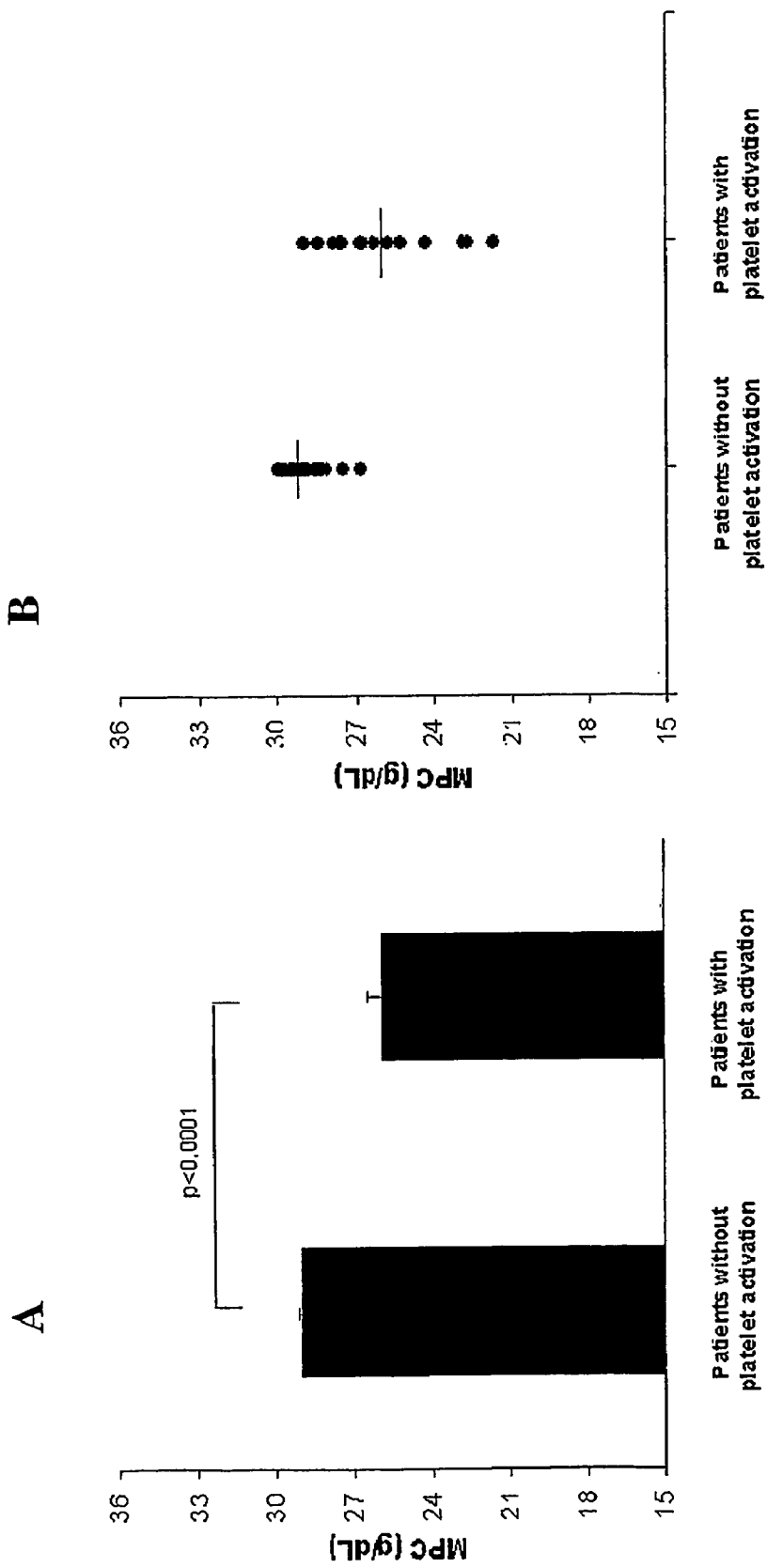
FIGS. 3A and B provide graphical depictions of measured mean and individual values of mean platelet concentration (MPC) in patients without and with elevated baseline levels of platelet activation, respectively.
Figure 4:
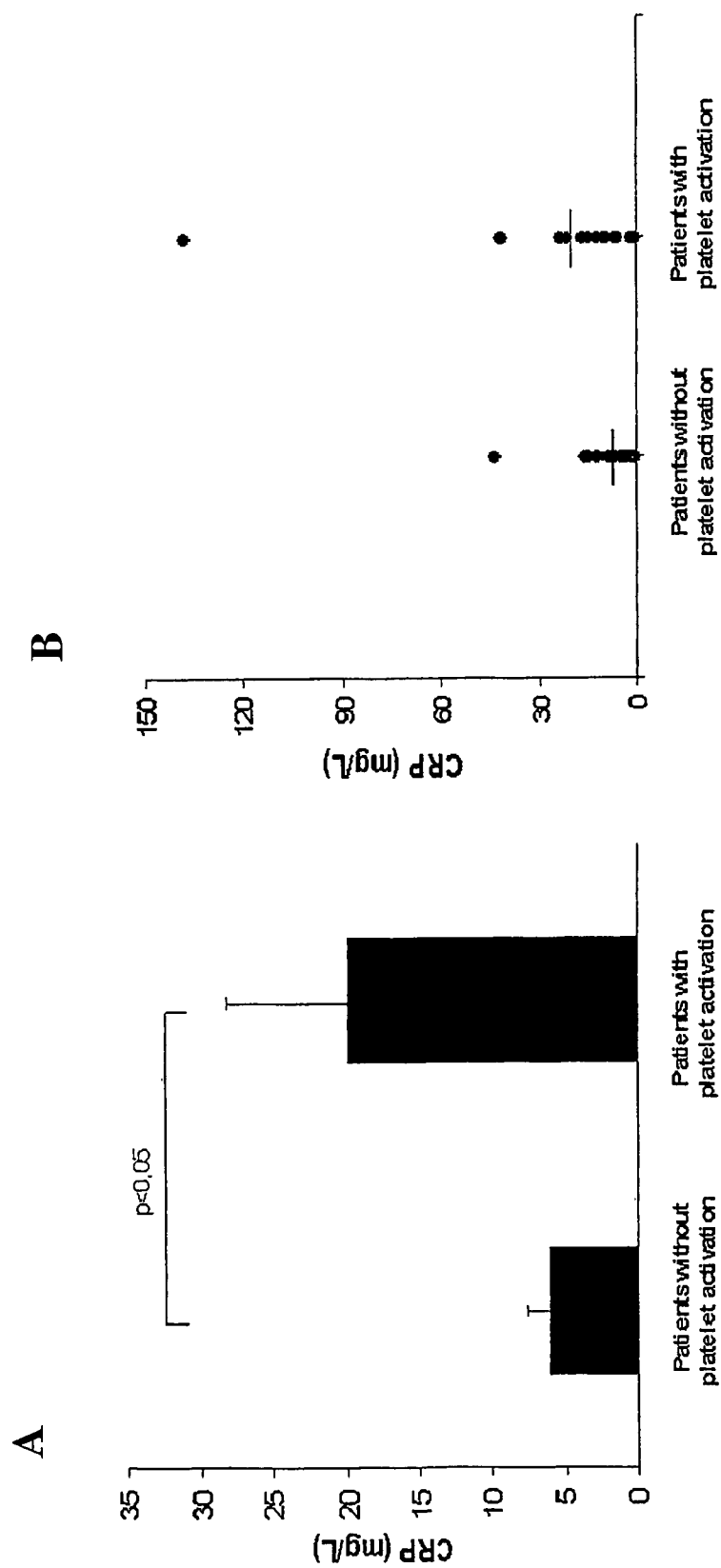
FIG. 4 provides graphical depictions of measured mean and individual values of C-reactive protein (CRP) in patients without and with elevated baseline levels of platelet activation, respectively.

Relationship between baseline platelet activation and CRP levels. In Group 1 (no detectable platelet activation before and after treatment) the MPC values were significantly greater compared to Group 2 (platelet activation upon admission and positive response to treatment) (28.95±0.74 g/dL, n=28 vs. 25.94±2.10 g/dL, n=16, $p<0.0001$, respectively) (Table 3; FIGS. 3A and 3B). The CRP concentrations were increased in Group 2 compared to Group 1 (6.02±8.64 mg/L vs. 19.89±33.14 mg/L ($p<0.05$) (Table 3; FIGS. 4A and 4B).

TABLE 3

Baseline platelet activation and CRP levels in the two groups of patients.

| | Basal platelet activation | | |
|---|---|---|---|
| | Group 1 (n = 28) | Group 2 (n = 16) | |
| MPC (g/dL) | 28.95 ± 0.74 | 25.94 ± 2.10 | $p < 0.0001$ |
| | (26.80-29.95) | (21.70-28.90) | |
| CRP (mg/L) | 6.02 ± 8.64 | 19.89 ± 33.14 | $p < 0.05$ |
| | (0.53-43.25) | (0.40-138) | |

Values are expressed as the mean ± SD. MPC = mean platelet component concentration.

We observed that platelet activation and CRP levels are significantly ($p<0.001$) related such that 81% of patients in Group 2 had high CRP concentrations (≧6.11 mg/L) compared to 29% of patients in Group 1 (Table 4).

TABLE 4

Relationship between platelet activation and inflammation

| | Platelet activation | | |
|---|---|---|---|
| CRP (mg/L) | + (n = 16) | 0 (n = 28) | |
| ≧6.11 | 13 | 8 | $p < 0.001$ |
| <6.11 | 3 | 20 | |

Sensitivity 71.4%; Specificity 81.3%

The foregoing Example demonstrated a heterogeneous relationship between platelet activation and elevated CRP in patients with acute coronary syndrome. Platelet activation was evaluated by surface expression of platelet activation marker, CD62P measured on the ADVIA 120 Hematology System. MPC decreased with platelet activation and is associated with decreased platelet density linked to platelet degranulation. The measurement of MPC is an advantageous strategy in that it does not require specimen preparation, platelet activation specific receptors, or activation-specific receptor labels. The MPC values showed very good inverse correlation with the percentage of platelets expressing CD62P antigen as detected by fluorescent flow cytometry after activation by thrombin. It was also observed that platelet activation and levels of a representative early platelet inflammation marker, CRP, are significantly related; these results demonstrated a greater basal platelet activation in patients with the exemplary platelet-affected pathology ACS, manifested as elevated baseline CRP levels.

This Example demonstrated a novel and medically-significant use for the STC parameter that fills the unmet need for an early marker of platelet-affected vascular pathologies, and that the MPC marker may be used alone, or in conjunction with other early markers of platelet activity, for example, the highly-sensitive C-reactive protein and/or other markers of adverse cardiovascular events, such as BNP, d-Dimer, or Troponin I, for such early indication.

In addition, the Example validated the use of the MPC parameter (again, alone or in conjunction with other markers of platelet activation, such as, for example, CRP or P-selectin) and the determination of individual patients' baseline platelet activation status to identify patients who would likely produce a material response to aggressive anti-platelet regimens and would therefore benefit from such therapeutic strategies.

Example 2

Variability in Platelet Response to Anti-Platelet Therapies in Patients with Acute Coronary Syndrome and Undergoing Angioplasty This study established the clinical usefulness of a novel method for evaluating platelet activation and the variability in platelet response to platelet antagonist therapy in patients undergoing percutaneous transluminal coronary angioplasty. It also illustrated the use of platelet-activation markers to define high-risk patients and to monitor the platelet response of individual patients to anti-platelet therapies, either concurrently with angioplasty or alone.

Patients. A total of 44 patients who underwent elective percutaneous coronary angioplasty and stenting were evaluated Patients were enrolled in the study after informed consent had been obtained. Their baseline variables including age, gender, smoking history and medication were documented. The treatments were assigned based on the angiographic characteristics. Patients with presence of thrombus and high risk vessel disease were assigned to Abciximab. Two thirds (n=29) of patients received a loading dose of Clopidogrel (300 mg) before the beginning of the PTCA procedure followed by 75 mg daily for 1 month. One third (n=15) of patients received a 0.25 mg/kg bolus of Abciximab intravenously before the beginning of the PTCA procedure followed by a 0.125 µg/kg/min infusion for 12 h. These patients also received Clopidogrel a designated number of hours after PTCA.

Reagents. Platelet control, mouse $IgG_1$ PE; Platelet control mouse $IgG_1$ FITC; monoclonal antibodies, CD61a (GPIIIa) FITC-conjugate; CD62P-PE-conjugate; and CaliBRITE beads were purchased from Becton Dickinson Immunocytometry Systems (San Jose, Calif.). Dulbecco's PBS (PBS) was obtained from Gibco/BRL (Cat. No. 14040, Grand Island, N.Y.). Formaldehyde, 10% Ultra-pure Methanol-free was obtained from Polyscience (Cat. No. 04018, Warrington, Pa.). ADVIA 120 Hematology OPTIpoint, SETpoint calibrator, TESTpoint controls, Low, Normal, and High were obtained from Bayer HealthCare, LLC (Tarrytown, N.Y.).

Other materials. VACUTAINER $K_2$EDTA tubes were obtained from Becton Dickinson VACUTAINER Systems (Franklin Lakes, N.J.). Instrumentation:FACScan:PowerPC Macintosh G3/300 MHZ, equipped with an argon laser, and Lysis II analysis software from Becton Dickinson Immunocytometry Systems (San Jose, Calif.). Bayer's ADVIA 120 Hematology System and Bayer's Customized Proprietary Refractive Index Series Software were acquired from Bayer HealthCare, LLC, Diagnostics Division (Tarrytown, N.Y. and Dublin, Ireland).

Collection of blood. Blood was drawn with a 21-gauge needle into EDTA (5 mM) tubes, mixed immediately with the anticoagulant, and avoiding frothing during the mixing procedure. The first 1-2 ml of blood were discarded to avoid the effects and traces of thrombin generated during venipuncture. Universal precautions were taken at all times during phlebotomy. Whole blood specimens for measurement of the ADVIA 120 System platelet parameters and CD62P-PE flow cytometry analysis were taken prior to baseline, 2 h, 5 h, and 24 h after administration of a loading charge of Clopidogrel and percutaneous transluminal coronary angioplasty (PTCA), and prior to, 10 min, 2 h, and 24 h after administration of the Abciximab bolus and PTCA. All specimens were processed within 1 h after blood collection.

Fluorescence flow cytometry analysis. Whole blood samples were fixed with methanol-free paraformaldehyde (final concentration 0.5%). Fixed blood samples (5 µl) were incubated at room temperature for 15 min in the dark with monoclonal antibody CD61a-FTTC (10 µl) to identify the platelets and CD62P-PE (10 µl) to measure the expression of P-selectin. Platelets labeled with FITC- or PE-conjugated isotype control antibody were used as control for nonspecific staining. Samples were diluted to 1 ml with PBS. FACScan calibration and compensation were performed as recommended by the manufacturer. Five thousand (5,000) CD61a positive events were acquired on the FACScan flow cytometer equipped with Lysis II software. Data analysis was performed using a threshold based on the FITC-fluorescence correlating to the platelet specific binding of CD61a-FITC antibodies. A gate was drawn around the fluorescent platelet population. The CD61a-FITC labeled platelets that were also positive for PE-conjugated activation marker antibody (CD62P) were quantized and presented, expressed as percentage of positive events.

Bayer ADVIA 120 Automated Hematology System platelet density measurement. The two-dimensional platelet method is based on the analysis of platelets from whole blood by flow cytometry using the ADVIA 120 (Chapman E. S. et al., *Thromb. Haemost.* (2003) 89:1004-1015), The system is linear for MPC values where the reference normal mean is 27.2±1.3 g/dL (Brummitt D. R. and H. F. Barker. *Clin. Lab. Haem.* (2000) 22:103-107). The system was standardized and calibrated as per manufacturer's instructions. The ADVIA 120 Hematology System was quality controlled using TESTpoint Hematology control reagents (Bayer HealthCare, LLC, Tarrytown, N.Y.). The whole blood specimens anticoagulated with EDTA were processed within 1 h after specimen collection. The ADVIA 120 platelet density parameter, MPC, was acquired as a measure of baseline platelet activation, and 10 min, 2 h, 5 h, and 24 h after anti-platelet drug therapy.

Statistical analysis. Platelet CD62P expression and MEC were compared using the paired t-test to test for significant differences for repeated measures. To control for potential errors introduced by deviations from normal distribution, we validated the results of the t-test by the Friedman's test followed by the Wilcoxon's matched pairs signed ranks test. The nonparametric tests always confirmed the results of parametric tests. P values <0.05 were considered statistically significant.

Results

Baseline characteristics of patients. Clinical and demographic features of study patients are shown in Table 5. All patients had symptomatic coronary artery disease, unstable angina and/or myocardial infarction. The majority of patients had received aspirin before hospitalization.

TABLE 5

Clinical and demographic characteristics of patients

|  | Clopidogrel n = 29 | Abciximab n = 15 |
|---|---|---|
| Sex | M: 21; F: 8 | M: 13; F: 2 |
| Age | 60 ± 13 | 59 ± 10 |
| Diagnosis | Number (%) | Number (%) |
| UA | 23 (79) | 8 (53) |
| MI | 6 (21) | 6 (40) |
| Stable coronary artery disease | 0 | 1 (7) |
| Medication received before | | |
| Aspirin or entrophen | 26 (90) | 13 (86) |
| Oral anticoagulant | 16 (55) | 10 (66) |
| History | | |
| Hypertension | 13 (45) | 8 (53) |
| Diabetes | 3 (10) | 1 (6) |
| Current Smoking | 11 (38) | 5 (33) |
| Previous Smoking | 2 (7) | 0 |
| Prior PTCA | 8 (28) | 4 (27) |
| Prior CABG | 1 (3) | 3 (20) |

Platelet activation status in patients receiving Clopidogrel and Abciximab. In the population of Clopidogrel patients (n=29), mean CD62P expression levels decreased significantly after treatment (means±SE, 9.5±3.3%, 3.1±1.8%, 1.2±0.7% and 1.8±1.1%, for baseline, 2 h, 5 h, and 24 h, respectively) (FIG. 5B). Correspondingly, mean MPC levels increased (means±SE, 27.8±0.4 g/dL, 28.4±0.3 g/dL, 28.9±0.2 g/dL and 28.7±0.2 g/dL, n=29, for baseline, 2 h, 5 h, and 24 h, respectively) (FIG. 5A).

Figure 6:
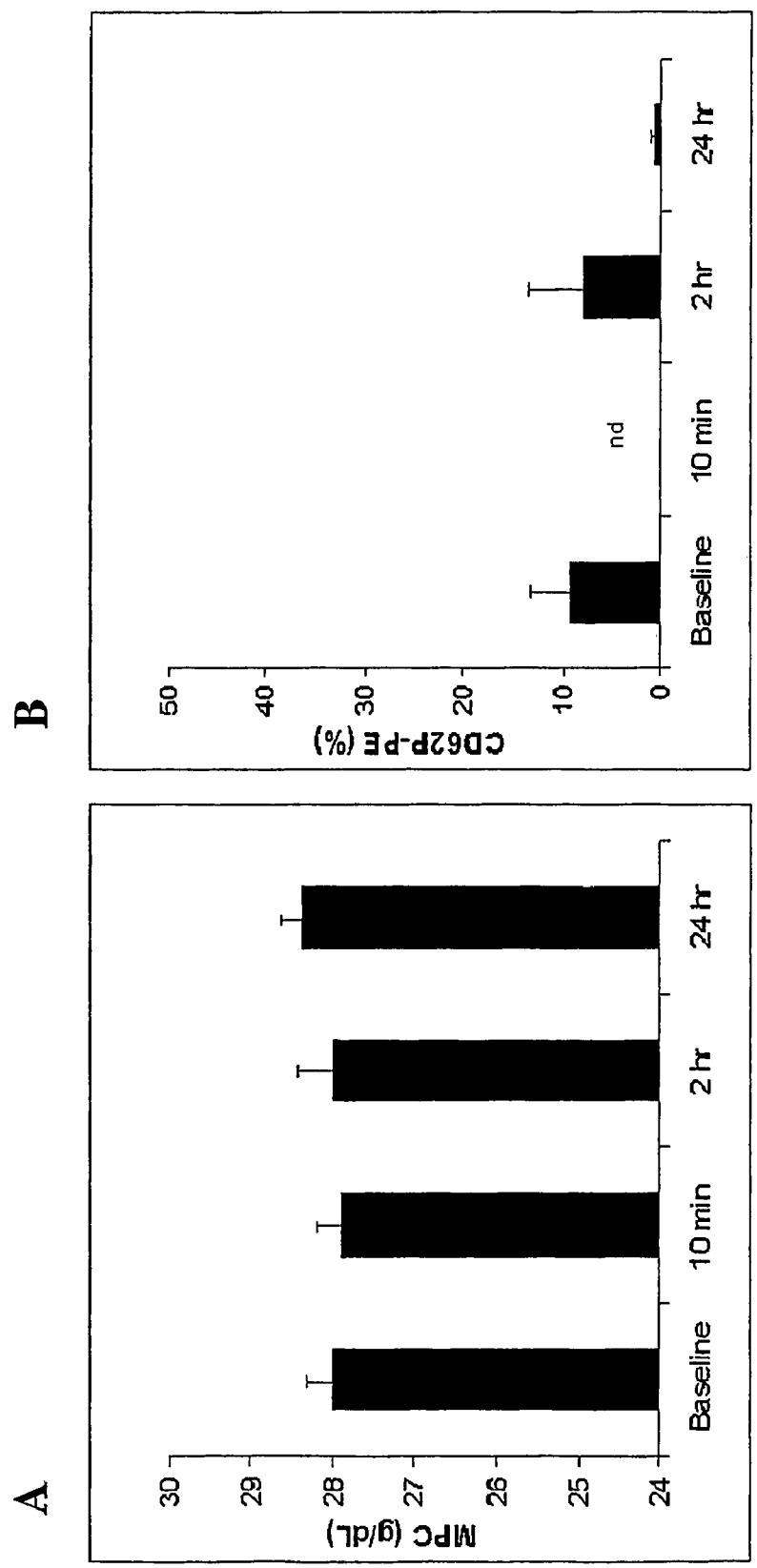

In the population of abciximab patients (n=15), similar results were seen. CD62P expressions were (mean±SE) 9.3±4.0%, 7.9±5.4% and 0.7±0.3%, for baseline, 2 h, and 24 h, respectively (FIG. 6B), and MPC levels were (mean±SE) 28.0±0.3 g/dL, 27.9±0.3 g/dL, 28.0±0.4 g/dL and 28.4±0.2 g/dL, for baseline, 10 min, 2 h, and 24 h, respectively (FIG. 6A).

Individual platelet activation determinations in patients receiving either clopidogrel or abciximab demonstrated heterogeneity of platelet activation. The patients were characterized based on the combination of the baseline platelet activation parameters, MPC and CD62 expression, and the response to the anti-platelet therapy. For our population, we have already reported a normal MPC value, 27.9±0.9 (Ahnadi C. E. et al., *Thromb. Haemost.* (2003) 90:940-948). In a larger set of data (n=51), the MPC in normal healthy donors was 28.1±1.0 g/dL (data not published). The CD62P-PE % positive events was <2% for normal healthy donors (Ahnadi C. E. et al., *Thromb. Haemost.* (2003) 90:940-948).

Patients were characterized either by high platelet activity upon admission and positive response to treatment, or by no detectable platelet activation before or after treatment. Several patients (n=7) demonstrated platelet activation levels that were normal upon admission, and became activated after treatment and surgical intervention.

Figure 7:
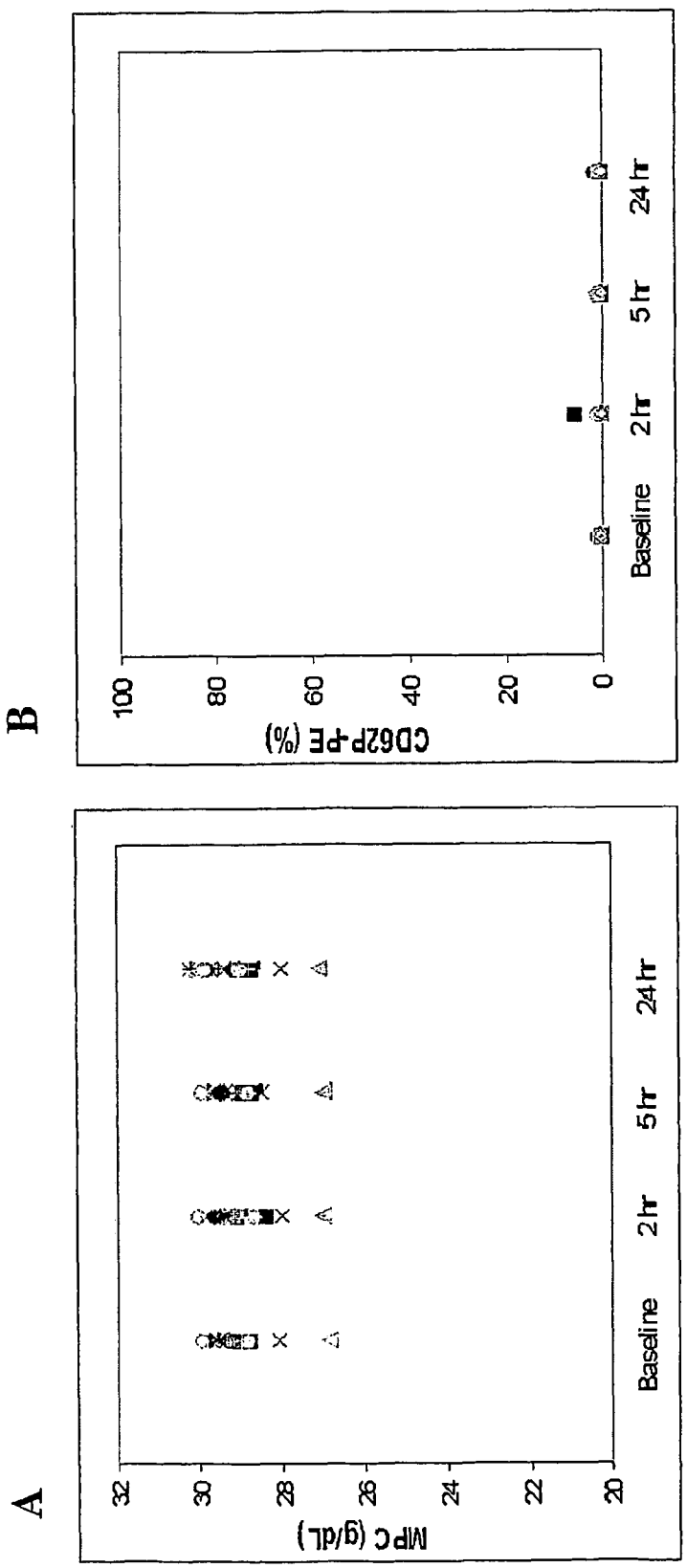

Patients who exhibited high baseline platelet activation responded to Copidogrel treatment as indicated by a decrease in CD62P percent positive expression at time points after treatment ((mean±SE) 23.4±6.6%, 2.0±1.0%/, 0.3±0.1% and 1.5±0.5%, p<0.01, for baseline, 2 h, 5 h, and 24 h, respectively). A concomitant increase in MPC values (25.7±0.8 g/dL, 28.0±0.5 g/dL, 28.8±0.3 g/dL and 28.4±0.3 g/dL, p<0.01, for baseline, 2 h, 5 h, and 24 h, respectively) was seen in those patient samples. Individual changes in MPC and CD62P values of patients with and without baseline activated platelets are presented in FIGS. 7 and 8, respectively (each individual patient is represented by a different symbol, showing the change in platelet activation in response to treatment with Clopidogrel). Similar patterns to those found in Clopidogrel patients were observed in Abciximab patients.

Figure 9:
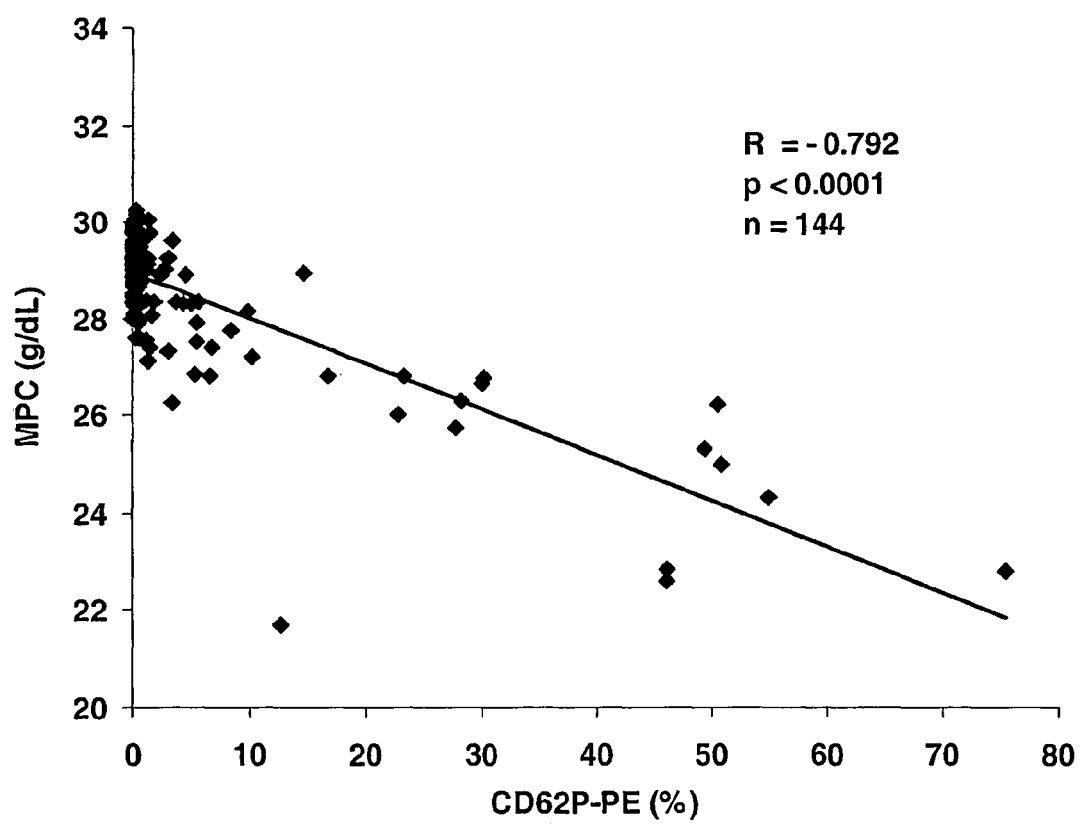
FIG. 9 depicts the found correlation between the platelet activation parameter MPC measured by the ADVIA 120 Hematology System and the percent positive (% F) CD62P-PE events determined by fluorescence flow cytometry.

Correlation between MPC and CD62P. The correlation between fluorescence surface marker expression of CD62P-PE and the activation state determined by the change in MPC is shown in FIG. 9. The correlation included the platelet activation values for baseline and for the response to anti-platelet therapy. Increased percentage CD62P-positive platelets are strongly correlated with decreased MPC values (r=−0.792, p<0.0001, n=144). An unexpected high CD62P-PE value (75%) was observed in one patient at 2 hours after Abciximab and angioplasty. The corresponding MPC value was very low (22.8 g/dL) indicating high level of platelet activation. The baseline CD62 and MPC were 4.2% and 28.3 g/dL respectively. This patient had some complications of pacemaker installation and did not finish the 24-hour sampling.

Important implications for clinical use. The preceding findings indicate that early detection of platelet activation status may be useful for identifying patients with confirmed cases of vascular disease states who would benefit from platelet antagonist therapy. Inter-individual variation in response to anti-platelet therapy and clinical risk of thrombosis or bleeding associated with these treatments have been reported. See Aguirre F. V. et al., *Circulation* (1995) 91:2882-2890; Bihour C. et al., *Arterioscler. Thromb. Vasc. Biol.* (1999) 16: 212-219; Kleiman N. S. et al., *J. Am. Coll. Cardiol.* (1995) 26:1665-1671). However, predictive methods such as those described herein had not elsewhere been developed. Currently, decisions for anti-platelet treatment are based on clinical data but not on platelet activation studies in individual patients. In addition to the need for methods for predicting individual response to platelet antagonist therapy, there is a well-recognized need, once treatment has been elected, for clinically applicable methods to monitor platelet function in the treatment and prevention of platelet-affected disease states.

The present Example was designed to establish the correlations among, and to evaluate the clinical usefulness of, these parameters to measure the magnitude of baseline platelet activation, as well as to follow anti-platelet therapy in patients with a vascular disease state, and who were also undergoing coronary angioplasty. Our data showed a close correlation between CD62P-PE expression and MPC as measured on the ADVIA 120 Hematology System. Individual platelet activation determinations in patients receiving either Clopidogrel or Abciximab showed heterogeneity of platelet activation as assayed by MPC and CD62P-PE expression. Patients were characterized as having either high platelet activity upon admission and positive response to treatment or no detectable platelet activation before or after treatment. In the group of patients with the greatest baseline platelet activation, response to Clopidogrel exhibited a significant reduction in platelet activation as determined by both CD62P decrease and platelet density change expressed by increasing MPC. It has been shown that clopidogrel suppresses expression of platelet activation markers CD62, CD63, and PAC-1 after stimulation with ADP or thrombin in healthy subjects (Schomig A. et al., *N. Engl. J. Med*. (1996) 334:1084-1089) and in patients after myocardial infarction (Moshfegh K. et al., *J. Ant. Coll. Cardiol*. (2000) 36:699-705). In our study, the majority of patients, including patients with increased baseline platelet activation, received aspirin therapy. The platelet inhibition effect of aspirin was not demonstrated by the classic or new platelet activation measurements reported by this study. The apparent lack of aspirin effect may be in part due to the aspirin resistance phenomena. Several clinical trials suggest that there are individual differences in the response to aspirin dose used in clinical trials (Serebruany V. L. et al., *Am. Heart J*. (2001) 142:611-616) and influence of genetic polymorphisms (Nurden A. T. *Thromb. Haemost*. (1995) 74:345-351). Other investigators, using other methods to measure platelet activation, have reported similar variability of platelet activation in patients with coronary artery diseases. See, e.g., Serebruany V. L. et al., *Amt. Heart J*. (1998) 136:398-405; Gurbel P. A. et al., *Thromb. Res*. (2000) 99:105-10.

These observations cast into doubt whether clinicians should uniformly use aggressive and costly anti-platelet strategies without individual assessment of platelet status in patients with vascular pathologies, and the present invention makes possible such individual assessment. Patients who exhibit activated platelets would seem to be ideal candidates for aggressive anti-platelet strategies (since a material response to therapy may be predicted, and an increased risk of negative cardiac events is indicated), whereas patients with diminished or absent platelet activity would be expected to derive less benefit and could be at greater risk for bleeding complications. Furthermore, the use of the MPC parameter for anti-platelet therapy monitoring was shown here to provide rapid access to platelet activation test results and to aid in detecting the heterogeneity of platelet activation among patients with platelet-affected disease states, which, in the present Example, correlated with the variability of patient response to treatment.

Example 3

Mean Platelet Component as a Biomarker for Risk Stratification for Patients with Vascular Conditions Novel serum biomarkers are needed for diagnosis of patients with platelet-affected vascular pathologies, including unstable angina. Decreased levels of MPC are associated with platelet activation and may be a maker for such patients. In the absence of a definitive biomarker, diagnosis is made on clinical grounds. Untreated patients with unstable angina have a. high likelihood of death, myocardial infarction, or need for urgent revascularization in the very near term (for example, within less than six months). The following study was designed to establish that for patients who present to the hospital emergency department with chest pain, a low mean platelet component is associated with increased risk for adverse events. The study also investigated the association between BNP expression and increased risk.

Materials and methods. Blood was collected at presentation into tubes containing EDTA from 82 emergency department patients who presented with chest pain. The blood was tested within 30 min for mean platelet component using the ADVIA 120 hematology analyzer (Bayer Diagnostics, Tarrytown, N.Y.). An MPC of <25 g/dL was considered abnormal. After analysis, the samples were centrifuged and the plasma separated, aliquoted, and frozen at −70° C. These samples were thawed and tested for B-type natriuretic peptide (BNP) using either Triage (Biosite Diagnostics, San Diego, Calif.) or ADVIA Centaur (Bayer Diagnostics). A cutoff of 100 ng/ml was used in both assays.

Results. Eight (8) patients suffered an adverse event within six months. The MPC was abnormal (decreased below the expected basal level) in four of these eight patients (50%). For the remaining 73 patients who did not report an adverse event, the MPC was abnormal in 4 (5%). Using logistic regression analysis, the odds ratio for MPC for risk stratification was 3.56 (95% CI:0.8-15.9). The results did not reach statistical significance because of the low numbers of subjects enrolled. On a subset of these patients, the BNP concentration was abnormal in 4 of 6 patients (66%) who suffered an adverse event and 11 of 76 (14.5%) of those who did not have an adverse event. The odds ratio for BNP for risk stratification was statistically significant at 11.8 (1.9-72.5). When the two tests were combined, 4 out of the 4 (100%) on whom data available had an abnormal result for either MPC or BNP for those patients who suffered an adverse event. However, there was an increase in the number of patients who were positive for either test, 22 of 45 (49%), in the absence of an adverse event. The odds ratio for this combination cannot be computed.

Implications. Both the mean platelet component and BNP tests provide a useful measure for risk stratification among patients who present to the emergency room with chest pain or otherwise display risk factors for adverse events. The concurrent performance of these tests enabled the identification of a higher percentage of patients who were deemed to be at high risk, albeit at the expense of specificity. MPC status is thus predictive of future platelet activity accompanied by vascular complications and therefore also identifies individual patients who would be most likely to benefit from anti-platelet regimens by experiencing efficacious results. The predictive value of the MPC test may be enhanced by concurrent measurement of the expression of an early biomarker for vascular events.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for monitoring patients for efficacy of an anti-platelet therapy regimen comprising: determining a plurality of Mean Platelet Component ("MPC") values in a patient blood sample over time wherein said MPC values correspond to said patient's levels of platelet activation, and wherein an increase in said MPC values over time indicates a therapeutic effect of said therapy in said patient.

2. The method of claim 1 wherein an increase in MPC value to 25-30 g/dL or more indicates a reduction of platelet activation and a therapeutic effect in said patient.

3. The method of claim 1 wherein an increase in MPC value to 26-29 g/dL or more indicates a reduction of platelet activation and a therapeutic effect in said patient.

4. The method of claim 1 wherein an increase in MPC value to 27-28 g/dL or more indicates a reduction of platelet activation and a therapeutic effect in said patient.

5. The method of claim 1, wherein said patient is an angioplasty patient.

* * * * *